(12) United States Patent
Fang et al.

(10) Patent No.: US 11,015,192 B2
(45) Date of Patent: May 25, 2021

(54) METHOD FOR GENERATING A STRANDED RNA LIBRARY

(71) Applicant: QIAGEN GMBH, Hilden (DE)

(72) Inventors: Nan Fang, Neuss (DE); Wolfgang Krebs, Hilden (DE); Isabell Czolkos, Hilden (DE)

(73) Assignee: QIAGEN GMBH, Hilden (DE)

( * ) Notice: Subject to any disclaimer, the term of this patent is extended or adjusted under 35 U.S.C. 154(b) by 196 days.

(21) Appl. No.: 16/094,783

(22) PCT Filed: Apr. 20, 2017

(86) PCT No.: PCT/EP2017/059412
§ 371 (c)(1),
(2) Date: Oct. 18, 2018

(87) PCT Pub. No.: WO2017/182578
PCT Pub. Date: Oct. 26, 2017

(65) Prior Publication Data
US 2019/0119671 A1 Apr. 25, 2019

(30) Foreign Application Priority Data
Apr. 20, 2016 (EP) .................. 16166179.8

(51) Int. Cl.
*C12N 15/10* (2006.01)
*C12Q 1/6869* (2018.01)
(Continued)

(52) U.S. Cl.
CPC ..... *C12N 15/1093* (2013.01); *C12N 15/1096* (2013.01); *C12Q 1/6806* (2013.01); *C12Q 1/6869* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 2015/0203906 A1* | 7/2015 | Betts et al. | C12N 15/1096 435/6.12 |
| 2018/0230527 A1* | 8/2018 | Fang et al. | C12Q 1/6869 |

FOREIGN PATENT DOCUMENTS

| | | |
|---|---|---|
| WO | WO-91/006678 A1 | 5/1991 |
| WO | WO-98/044151 A1 | 10/1998 |

(Continued)

OTHER PUBLICATIONS

Beaucage et al. "Deoxynucleoside phosphoramidites—A new class of key intermediates for deoxypolynucleotide synthesis", 1981, Tetrahedron Letters 22 (20):1859-1862.
(Continued)

*Primary Examiner* — Kaijiang Zhang
(74) *Attorney, Agent, or Firm* — Ballard Spahr LLP (57) ABSTRACT

The invention relates to a method for preparing a strand-specific library from an nucleic acid or preferably RNA sample, for RNA comprising the steps of: (i) optionally fragmenting said RNA sample, (ii) generating a plurality of first cDNA strands by subjecting said fragmented RNA to reverse transcription by using a reverse transcriptase and first oligonucleotide primers, (iii) generating a plurality of second cDNA strands by using a DNA polymerase, second oligonucleotide primers, and the plurality of first cDNA strands, and (iv) ligating adapters to the 3' and 5' termini of the of double-stranded cDNA, (v) wherein the first cDNA strand allows no adapter ligation at its 5' terminus and said second cDNA strand allows adapter ligation at its 5' terminus, or vice versa, and, (v) optionally cloning, sequencing or otherwise using the strand-specific library. The invention also relates to a kit for preparing a strand-specific library from an RNA sample, wherein said kit comprises, (i) random oligonucleotide primers comprising a 5' terminus nucleotide which allows no adaptor ligation, (ii) random
(Continued)

oligonucleotide primers comprising a 5' terminus nucleotide which allows adaptor ligation, (iii) optionally a reverse transcriptase for synthesizing a first cDNA strand complementary to the template RNA, (iv) optionally dNTPs, and (v) optionally a DNA polymerase.

13 Claims, 3 Drawing Sheets

(51) Int. Cl.
*C40B 50/06* (2006.01)
*C12Q 1/6806* (2018.01)

(56) References Cited

FOREIGN PATENT DOCUMENTS

| WO | WO-2014118377 A2 * | 8/2014 | ........... C12Q 1/6844 |
|---|---|---|---|
| WO | WO-2014/150435 A1 | 9/2014 | |

OTHER PUBLICATIONS

Borodina et al.: "A strand-specific library preparation protocol for RNA sequencing", 2011, Methods in Enzymology, 500:79-98.

Lee et al. "RNaseIII and T4 Polynucleotide Kinase sequence biases and solutions during RNA-seq library construction", 2013, Biology Direct 8:16.

Li and Dewey "RSEM: accurate transcript quantification from RNA-Seq data with or without a reference genome" 2011, BMC Bioinformatics 12:323.

Lillehaug, et al., "Kinetics and specificity of T4 polynucleotide kinase", 1975, Biochemistry 14(6):1221-1225.

Parkhomchuk et al. "Transcriptome analysis by strand-specific sequencing of complementary DNA", 2009, Nucleic Acids Research 37(18):e123.

Podnar et al., "Next-generation sequencing RNA-Seq library construction", 2014, Current Protocols in Molecular Biology, No. SUPL.106.

Ronaghi et al. "Real-time DNA sequencing using detection of pyrophosphate release". 1996, Analytical Biochemistry 242(1):84-89.

Van Houten et al. "Labeling Efficiency of Oligonucleotides by T4 Polynucleotide Kinase Depends on 5'—Nucleotide", 1998, Anal. Biochemistry 265(2):386-389.

Wang et al., "A Low-Cost Library Construction Protocol and Data Analysis Pipeline for Illumina-Based Strand-Specific Multiplex RNA-Seq", 2011, PLOS ONE, 6(10): e26426.

Wang et al. "Quality control of RNA-seq experiments" 2012, Bioinformatics, 28(16):2184-2185.

International Search Report and Written Opinion were dated Jun. 12, 2017 by the International Searching Authority for International Application No. PCT/EP2017/059412, filed on Apr. 20, 2017 and published as WO 2017/182578 dated Oct. 26, 2017 (Applicant—Qiagen GMBH) (9 Pages).

International Preliminary Report on Patentability was dated Oct. 23, 2018 by the International Searching Authority for International Application No. PCT/EP2017/059412, filed on Apr. 20, 2017 and published as WO 2017/182578 dated Oct. 26, 2017 (Applicant—Qiagen GMBH) (6 Pages).

\* cited by examiner

METHOD FOR GENERATING A STRANDED RNA LIBRARY

CROSS-REFERENCE TO RELATED PATENT APPLICATIONS

This application claims the benefit of priority under 35 U.S.C. § 371 of International Application No. PCT/EP2017/059412 filed on Apr. 20, 2017 which claims priority to European Application No. EP 16166179.8 filed on Apr. 20, 2016. The content of these earlier filed applications is hereby incorporated by reference in their entirety.

FIELD OF THE INVENTION

The present invention is in the field of molecular biology, in particular in the field of next generation sequencing. More in particular, the present invention relates to a method for generating strand-specific RNA library. The invention further comprises a composition for generating strand-specific RNA library and a kit thereof.

BACKGROUND

The high-throughput RNA sequencing (RNA-Seq) technology, enabled by the recent developments of the next generation sequencing, has become a powerful tool in analyzing gene expression profiles, detecting transcript variants and understanding the functions of the non-coding regulatory RNAs.

The information on the exact strand from which the RNA is transcribed is useful in discovering the anti-sense and non-coding RNA species and studying their functions. The ability to distinguish the sense transcripts from the overlapping anti-sense transcripts can also further improve the accuracy of the RNA quantification.

A standard RNA-Seq library is generated by ligating sequencing adaptors to double-stranded cDNA. The direction of the original transcripts cannot be inferred from sequencing such RNA-Seq libraries since the ligation is not directional.

There are various methods to generate strand-specific RNA-Seq libraries. The most commonly used method is based on the dUTP incorporation into the second strand cDNA prior to adaptor ligation. Following adaptor ligation, the second strand cDNA can be specifically digested by UNG enzyme so that only the library strand containing first strand cDNA will be sequenced and information on the direction of the transcripts can therefore be obtained (Parkhomchuk et al. 2009, Nucleic Acids Research 37 (18):e123).

The dUTP method has several drawbacks. First, the method requires one additional UNG digestion step following adaptor ligation, making the library construction process more complicated. Additionally, just like any enzyme reaction, the UNG reaction is not 100% efficient; therefore, there could be residual second strand cDNA even after UNG digestion that could cause false interpretation of the RNA-Seq data.

An alternative method for selecting a particular strand of RNA and/or producing a cDNA library has also been disclosed in the patent application WO 2014/150435. Said method comprises the use of a first tagged sequence consisting of a tagged random primer for the synthesis of the cDNA strand of the target nucleic acid and a second tagged sequence consisting of a double-stranded polynucleotide adaptor including a 3' overhang of randomized bases that is blocked on the 3' end. The second tagged sequence also comprises a phosphate group on the 5' end of the sequence that links to the cDNA strand generated by reverse transcription. The method disclosed in WO 2014/150435 also comprises additional steps such as the removal of the 3'-blocked complementary strand and subsequent hybridization of the cDNA strand to an adaptor that can hybridize to the second tagged sequence linked to the cDNA and allows the synthesis of the complementary cDNA strand by its extension.

However, the method disclosed in WO 2014/150435 presents some limitations since it requires the use of complex tagged primers, e.g. the double-stranded 3'-blocked tagged sequence. Further, additional enzymatic reactions after ligation of said tagged sequence are required to remove the 3'-blocked complementary strand and generate a single cDNA strand.

More in general, one disadvantage of RNA-seq is that sequence data can be biased by library construction steps such as reverse transcription, adaptor ligation or amplification. With reference to the adaptor ligation step, T4 Polynucleotide Kinase (T4 PNK) plays a key role; its kinase activity adds phosphate groups at 5' fragment ends, while its phosphatase activity removes phosphates from at 3' fragment ends and leaves hydroxyl groups. Although T4 PNK continues to be widely used, the enzyme exhibits two important limitations. First, T4 PNK exhibits base bias and the effectiveness of phosphorylation depends on the base at the 5'-end of the oligonucleotide target, with 5'-C exhibiting the lowest extent of phosphorylation (Van Houten et al. 1998, Anal. Biochemistry 265 (2):386-389). Second, T4 PNK can be challenging to use since precise enzyme titrations and careful optimization of reaction times are often required in order to achieve desired results (Richardson 1981, The Enzymes, 3rd Edition, Ed. P. D. Boyer, Academic Press, New York; Lillehaug and Kleppe 1975, Biochemistry 14 (6):1221-1225).

A solution to obviate this issue has been provided by USB Corporation that developed OptiKinase™, recombinant version of T4 PNK that has been genetically engineered for improved 5'-phosphorylation of oligonucleotides. Like native T4 PNK, OptiKinase catalyzes the transfer of the terminal phosphate of ATP to 5'-hydroxyl termini of oligonucleotides. However, unlike native T4 PNK which exhibits a bias against the efficient labelling of certain oligonucleotides, OptiKinase exhibits minor discrimination (Lee et al. 2013, Biology Direct 8:16).

In view of all the limitations and drawbacks of the current methods, it appears necessary to provide an improved method for generating strand-specific RNA library. The method disclosed herein is intended to solve the aforementioned issues characterizing the current methods.

SUMMARY OF THE INVENTION

A first aspect of the present invention relates to a method for preparing a strand-specific library from a nucleic acid sample, comprising the steps of:
i. fragmenting said nucleic acid sample,
ii. generating a plurality of first nucleic acid strands by subjecting said fragmented nucleic acid to a first specific amplification by using first oligonucleotide primers,
iii. generating a plurality of second nucleic acid strands by strand specific elongation using second oligonucleotide primers and the plurality of first nucleic acid strands, and iv. ligating adapters to the 3' and 5' termini of the double-stranded nucleic acid,
v. wherein the first cDNA strand allows no adapter ligation at its 5' terminus and said second cDNA strand allows adapter ligation at its 5' terminus and,
vi. optionally cloning, sequencing or otherwise using the strand-specific library Regarding step (v) it should be noted that this may also apply vice versa, i.e. wherein the first cDNA strand allows adapter ligation at its 5' terminus and said second cDNA strand allows no adapter ligation at its 5' terminus.

Another aspect of the present invention relates to a kit for preparing a strand-specific library from an RNA sample, wherein said kit comprises:
i. random oligonucleotide primers comprising a 5' terminus nucleotide which allows no adaptor ligation,
ii. random oligonucleotide primers comprising a 5' terminus nucleotide which allows adaptor ligation,
iii. optionally a reverse transcriptase for synthesizing a first cDNA strand complementary to the template RNA,
iv. optionally dNTPs,
v. optionally a DNA polymerase, and
vi. optionally a ligase.

DESCRIPTION OF THE INVENTION

There are two main methods for preparing strand-specific RNA sequencing libraries: one is sub-sequentially ligating different adaptors to the 3' and 5' ends of the RNA molecules (e.g. Ion Total RNA-Seq Kit v2 from Life Technologies); another, and more widely used method is incorporating dUTP in addition to dNTPs in the second strand cDNA synthesis; following adaptor ligation, the second cDNA strand is digested with UNG and removed (e.g., TruSeq Stranded mRNA Sample Prep Kit from Illumina).

The conventional methods have their drawbacks: for example, the RNA-ligation-based method is subject to the bias of the RNA ligases; while the dUTP-based method requires an additional enzymatic digestion step to remove the second, dUTP-containing strand, making the process more cumbersome and time-consuming than standard RNA-seq library prep methods.

Other limitations characterizing current RNA-seq methods may be intrinsically associated to its steps, such as reverse transcription, adaptor ligation or amplification. In particular, it has been observed that the 5' phosphorylation step of an oligonucleotide fragment by using T4 PNK may be affected by biased results (Van Houten et al. 1998, Anal. Biochemistry 265 (2):386-389).

Recently, an alternative method for preparing specific strand of RNA and/or producing a cDNA library has been disclosed in WO 2014/150435. However, said method is also limited by some drawbacks due to the use of complex tagged double-strand sequences for ligation and the requirement of additional steps for generating the target cDNA sequence.

Figure 1:
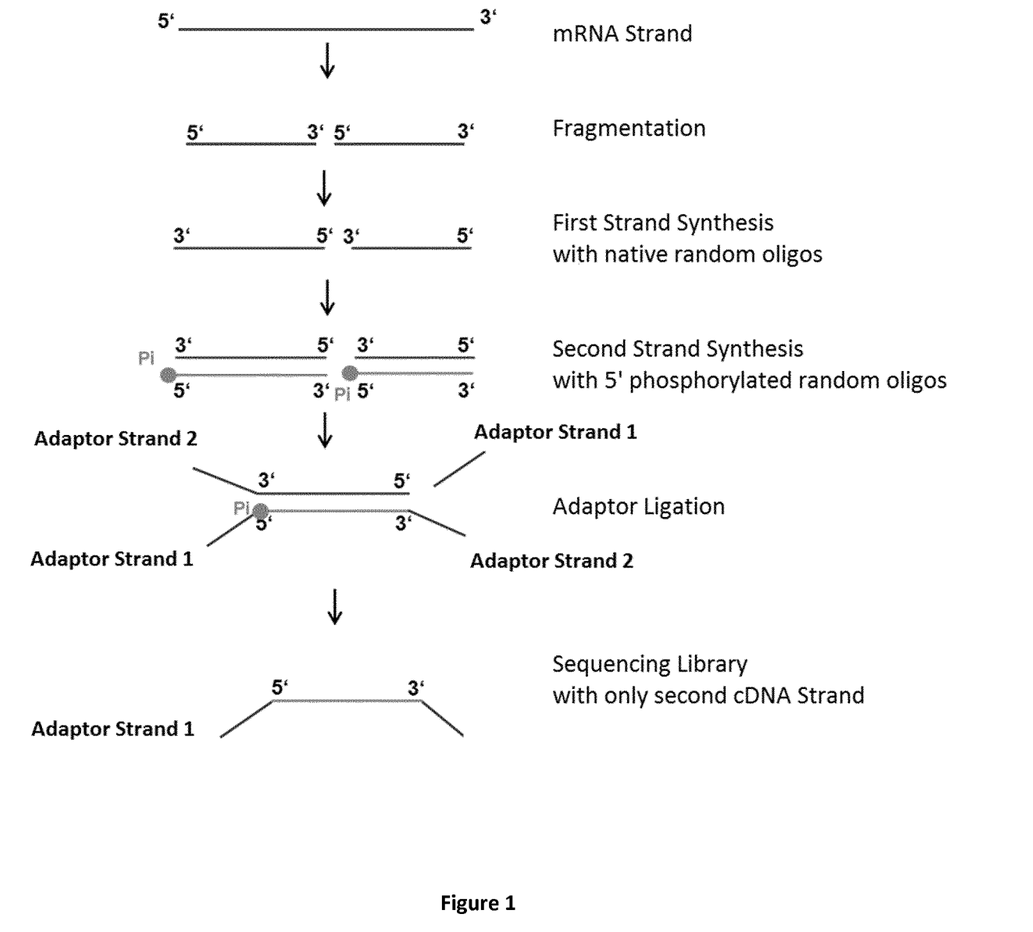
FIG. 1 shows the workflow for a stranded RNA sequencing library preparation.

The present invention provides an optimization of the current methods for generating a stranded RNA library, which comprises the use of 5'-modified, preferably 5'-phosphorylated random oligonucleotides as primers for the first or second strand cDNA synthesis. The 5' phosphorylation enables the direct ligation of the resulting cDNA strand to the sequencing adaptor, therefore only the cDNA strand generated with the 5'-phosphorylated random oligonucleotides, and not the complementary strand, will be ligated with the adaptor on both 5' and 3' ends and sequenced (FIG. 1 illustrates the workflow).

It will be appreciated by the person skilled in the art that the method disclosed in the present invention provides significant advantages over the prior art in terms of time and efficiency. In particular, it is worth noting that the use of 5'-modified, preferably 5'-phosphorylated random oligonucleotides, for generating strand-specific RNA libraries does not involve any additional enzymatic reaction steps in the workflow post-adaptor ligation. Moreover, as reported in the experimental part, the library generated by the present method showed good quality and even a higher percentage of mapped reads when compared to the un-stranded protocol. The stranded protocol with 90% uniquely mapped reads was compared to un-stranded (Ctrl) protocol with 82% uniquely mapped reads.

The method according to the present invention is also intended to overcome issues related to the use of T4 PNK before the ligation of adaptor to the target oligonucleotide sequences.

The invention relates to a method for preparing a strand-specific library from a nucleic acid sample, comprising the steps of (i) fragmenting said nucleic acid sample, (ii) generating a plurality of first nucleic acid strands by subjecting said fragmented nucleic acid to a first strand specific amplification (complementary DNA synthesis) by using first oligonucleotide primers, (iii) generating a plurality of second nucleic acid strands by strand specific elongation using second oligonucleotide primers and the plurality of first nucleic acid strands, and (iv) ligating adapters to the 3' and 5' termini of the of double-stranded nucleic acid, (v) wherein the first strand allows no adapter ligation at its 5' terminus and said second strand allows adapter ligation at its 5' terminus and, (vi) optionally cloning, sequencing or otherwise using the strand-specific library.

Regarding step (ii) a plurality of first nucleic acid strands is generated by annealing a first oligonucleotide primer to the fragmented nucleic acid sample obtained in step (i) and synthesizing the complementary nucleic acid strand by means of elongation of said first oligonucleotide primer. The synthesized double-stranded nucleic acid is then subjected to amplification to generate a plurality of first double-stranded nucleic acids as step (ii) demands.

Step (iii) is conceived analogously, wherein a plurality of second nucleic acid strands is generated by denaturation of the plurality of first double-stranded nucleic acids obtained in step (ii), annealing second oligonucleotide primers to the plurality of first nucleic acid strands, elongating said annealed second oligonucleotide primers.

Regarding steps (iv) and (v) the ligation of adaptors to the plurality of double-stranded nucleic acids obtained in step (iii) occurs specifically on one strand. This event is ensured by the presence of a phosphate group at the 5' terminus on a specific synthesized nucleic acid strand (i.e. first or second strand).

Therefore, according to a preferred embodiment of the first aspect of the present invention, the method disclosed herein does not comprise further enzymatic reactions in performing steps (iv) and (v). In a more preferred embodiment, the method disclosed herein does not comprise the use of a polynucleotide kinase, e.g. T4 PNK.

According to another embodiment of the first aspect of the present invention, only one nucleic acid strand allows adaptor ligation at its 5' terminus. This feature controls the strand-specificity of the method disclosed herein.

Regarding step (v) it should be noted that this may also apply vice versa, i.e. wherein the first cDNA strand allows adapter ligation at its 5' terminus and said second cDNA strand allows no adapter ligation at its 5' terminus.

In the context of the present invention, a specific class of nucleic acid may be, inter alia, RNA, DNA, cDNA (complementary DNA), LNA (locked nucleic acid), Peptide nucleic acid (PNA), mRNA (messenger RNA), mtRNA (mitochondrial RNA), rRNA (ribosomal RNA), tRNA (transfer RNA), nRNA (nuclear RNA), siRNA (short interfering RNA), snRNA (small nuclear RNA), snoRNA (small nucleolar RNA), scaRNA (Small Cajal Body specific RNA), microRNA, dsRNA (double-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA), snDNA (small nuclear DNA) or the like or any other class or sub-class of nucleic acid which is distinguishable from the bulk nucleic acid in a sample.

According to a preferred embodiment of the first aspect, the present invention relates to a method for preparing a strand-specific library from an RNA sample, comprising the following steps: (i) fragmenting said RNA sample, (ii) generating a plurality of first cDNA strands by subjecting said fragmented RNA to reverse transcription by using a reverse transcriptase and first oligonucleotide primers, (iii) generating a plurality of second cDNA strands by using a DNA polymerase, second oligonucleotide primers and the plurality of first cDNA strands, and (iv) ligating adapters to the 3' and 5' termini of the of double-stranded cDNA, (v) wherein the first cDNA strand allows no adapter ligation at its 5' terminus and said second cDNA strand allows adapter ligation at its 5' terminus, or vice versa, and, (vi) optionally cloning, sequencing or otherwise using the strand-specific library.

As used herein, the term "optionally" refers to the possibility that an event or circumstance may or may not occur. For example, in the context of the present application, the method disclosed herein may comprise or not the step of cloning, sequencing and/or otherwise using the strand-specific library.

In one embodiment of the present invention, the oligonucleotide primers of the present method comprise DNA, RNA and/or modified nucleotides. In the context of the present invention, "RNA" refers to both a single RNA strand and to a multiplicity of RNA strands. Accordingly, "DNA" refers to either a single-stranded DNA or double-stranded DNA and to a multiplicity of such DNA strands.

According to another embodiment of the present invention, the oligonucleotide primers are random oligonucleotide primers. As used herein, the term "random oligonucleotide primer" refers to a sequence not designed to be directed to a specific sequence in the nucleic acid sample to be amplified. In particular, a random oligonucleotide when used as a random primer represents a random mixture of oligonucleotide sequences, consisting of every possible combination of nucleotides within the sequence.

In the context of the present invention, a primer is capable of acting as a site of initiation of the synthesis or polymerization of a nucleic acid polymer, the sequence of which is complementary to the template strand, in the presence of nucleotides and an inducing agent such as DNA polymerase and at a suitable temperature and pH. The primer is preferably single stranded for maximum efficiency in amplification, but may alternatively be double stranded. If double stranded, the primer may be first treated, for example, by heating at a temperature sufficient to separate the strands, before being used to prepare extension products. Further, non-stringent conditions during hybridization may be used, which allow oligonucleotide primers to nonspecifically or randomly appose at many sites on the nucleic acid template where otherwise, under stringent hybridization conditions, those oligonucleotide primers would only hybridize to a specific site.

In the context of the present invention, the term first and second oligonucleotide primers are used for convenience solely for the purpose of identifying the different structure/function of the two primers.

In the context of the present invention, an adaptor refers to an oligonucleotide sequence, the ligation of which to a target nucleic acid strand allows the generation of amplification-ready products of said target nucleic acid strand. In the context of the present invention, the adaptors may be single or double-stranded. Preferably, the adaptors comprise double-stranded nucleic acids. As used herein the terms "adaptor and "adapter" can be used interchangeably.

Various adaptor designs are encompassed by the present invention. For example, in the event that adaptors comprise double-stranded nucleic acids, the two strands of the adaptor may be self-complementary, non-complementary or partially complementary. In some embodiments, the adaptor may comprise an indexing site. As used herein, the term "indexing site" refers to the possibility of informationally linking the sequences produced by parallel sequencing back to the sample from which they originate. Accordingly, the term "index" may be also interchangeably referred to as "barcodes" or "tags".

The adaptors may be oligonucleotides of known sequence and, thus, allow the use of strand specific library for amplification and/or sequencing of any polynucleotides to which both adaptors are appended or attached. The adaptors encompass also any oligonucleotides that may be marked and selected by any methods known in the art.

Further, the term "library" refers to a large number of nucleic acid fragments, here a collection of DNA fragments for sequencing analysis, which are generated from RNA. The libraries referred to herein are generated by optional fragmentation of a sample to be analyzed, reverse-transcription and generation of dsDNA, optional end-repairing, optional addition of a terminal adenine, and ligation of fragments and adapters when the ligation is not inhibited by a modified random oligonucleotide. Optionally, the purified DNA fragments are amplified and/or enriched before they are sequenced.

According to another embodiment of the present invention, the first or second oligonucleotide primers comprise a modification at their 5' terminal nucleotide. In the context of the present application, the first or second oligonucleotide primers are preferentially modified at the 5' terminus. As used herein, the term "preferentially modified" refers to a preferred modification indicating the presence of a phosphate group, an adenylation group (5'-rApp) or a derivative thereof at the 5' terminus.

According to another embodiment of the present invention, modification at 5' terminal nucleotide may comprise phosphate, adenylation group (5'-rApp), phosphorothioate, phosphoroselenoate or derivative group thereof.

According to a preferred embodiment, the first or second oligonucleotide primers are 5'-phosphorylated or 5'-adenylated oligonucleotides.

According to another embodiment of the present invention, the oligonucleotide primers may have a length between 6 and 30, 25, 20, or 10 bases. According to a preferred embodiment of the present application the oligonucleotide primers are composed by about 6-14 bases.

Oligonucleotide primers may be prepared using any suitable method, such as, for example, the phosphotriester and phosphodiester methods or automated embodiments thereof. In one such automated embodiment, diethylophosphoramidites are used as starting materials and may be synthesized as described by Beaucage et al. 1981, Tetrahedron Letters 22:1859-1862. One method for synthesizing oligonucleotides on a modified solid support is described in U.S. Pat. No. 4,458,066. It is also possible to use a primer which has been isolated from a biological source such as a restriction endonuclease digest.

Nucleic acid amplification is done using nucleotides NTPs or dNTPs. As used herein, the term "dNTP" refers to deoxyribonucleoside triphosphates. Non-limiting examples of such dNTPs are dATP, dGTP, dCTP, dTTP, dUTP, which may also be present in the form of labelled derivatives, for instance comprising a fluorescence label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methylcytosine, pseudouridine, dihydrouridine, 5-methylcytidine. Furthermore, ddNTPs of the above-described molecules are encompassed in the present invention.

As used herein, the term "NTP" refers to ribonucleoside triphosphates. Non-limiting examples of such NTPs are ATP, GTP, CTP, TTP, UTP, which may also be present in the form of labelled derivatives, for instance comprising a fluorescence label, a radioactive label, a biotin label.

In the context of the present invention, the biological sample from which RNA is extracted can be a sample of cells, tissue or fluid isolated from any prokaryotic or eukaryotic organisms or viruses. According to a preferred embodiment, the RNA is extracted from a eukaryotic organism.

According to another embodiment, said RNA sample comprises polyadenylated mRNA. In the context of the present invention, the polyadenylated tail may be of any length, so long as the tail is capable of hybridizing to a complementary oligonucleotide primer for the initiation of cDNA synthesis.

According to yet another embodiment, said RNA sample comprises RNA sample depleted of ribosomal RNA.

It is possible to amplify the library once it has been created. The most commonly used target amplification method is the polymerase chain reaction (PCR), which is based on multiple cycles of denaturation, hybridization of two oligonucleotide primers, each to opposite strand of the target strands, and primer extension by a nucleotide polymerase to produce multiple double stranded copies of the target sequence. Many variations of PCR have been described, and the method is being used for amplification of DNA or RNA nucleic acid sequences, sequencing, mutation analysis and others. Thermocycling-based methods that employ a single primer have also been described. Other methods that are dependent on thermal cycling are the ligase chain reaction (LCR) and the related repair chain reaction (RCR). Target nucleic acid amplification in the thermal cycling based methods is carried out through multiple cycles of incubations at various temperatures. Although these methods are widely used, amplification methods that use a thermocycling process have the disadvantage of long lag times which are required for the thermocycling block to reach the "target" temperature for each cycle. Consequently, amplification reactions performed using thermocycling processes require a significant amount of time to reach completion. In a preferred embodiment of the present invention the amplification of library is done with a method selected from the group comprising helicase dependent amplification (HDA), thermostable HDA (tHDA), strand displacement amplification (SDA), multiple displacement amplification (MDA), rolling circle amplification, single primer isothermal amplification (SPIA), restriction aided RCA, transcription mediated amplification (TMA), and amplification reactions using nicking enzymes, nicking enzyme amplification reaction (NEAR), amplification reactions using recombination proteins, recombinase polymerase amplification (RPA), reverse transcription.

In the context of the present invention, the method for preparing strand-specific library from an RNA sample comprises optionally a fragmenting step wherein the RNA sample may be fragmented by a variety of method including chemical, enzymatic, mechanical or thermal means. According to a preferred embodiment the RNA sample is fragmented by thermal, chemical means or a combination thereof.

One aspect of the present invention is directed to a method for generating a single stranded DNA library (e.g. cDNA library) from a starting RNA. The method involves the optional first step of fragmenting RNA to produce fragmented RNA. The fragmentation may produce RNA fragments of between 100 bases to 1000 bases in size. According to one embodiment of the present invention, the fragmented RNA sample comprises fragments of between 100 bp to 250 bp in size. According to one embodiment of the present invention, the fragmented RNA sample comprises fragments of between 100 bp to 500 bp in size. The fragments may be between 50 and 1000 bp.

According to another embodiment of the present invention, said method for preparing strand-specific library from an RNA sample comprise the step of generating a plurality of first cDNA strands by subjecting the fragmented RNA to reverse transcription by using a reverse transcriptase. In the context of the present invention, the reverse transcriptase comprises: retroviral reverse transcriptase, retrotransposon reverse transcriptase, hepatitis B reverse transcriptase, cauliflower mosaic virus reverse transcriptase, murine leukemia virus reverse transcriptase, avian myeoloblastosis virus (AMV), bacterial reverse transcriptase, Tth DNA polymerase and Taq DNA polymerase.

The libraries are preferably used in NGS sequencing. Several methods for DNA sequencing were developed in the mid to late 1990s and were implemented in commercial DNA sequencers by the year 2000. A first notable method for determining a DNA sequence has been disclosed in patent application WO 1991/006678, which describes a stepwise ("base-by-base") sequencing approach with removable 3' blockers on DNA arrays (blots and single DNA molecules). In 1996, Nyrén and co-workers published a real-time DNA sequencing method using detection of pyrophosphate release (pyrosequencing) (Ronaghi et al. 1996, Analytical Biochemistry 242 (1):84-89). Later, Mayer and Farinelli filed a patent WO 1998/044151 describing DNA colony sequencing. The DNA sample preparation and random surface-PCR arraying methods described in WO 1998/044151, coupled to the sequencing method disclosed in WO 1991/006678, are now implemented in Illumina's Hi-Seq genome sequencers. Lynx Therapeutics published and marketed "Massively parallel signature sequencing" (MPSS) in 2000. This method incorporated a parallelized, adaptor/ligation-mediated, bead-based sequencing technology and served as the first commercially available "next-generation" sequencing method. In 2004, 454 Life Sciences marketed a parallelized version of pyrosequencing. The first version of their machine reduced sequencing costs 6-fold compared to automated Sanger sequencing, and was the second of the new generation of sequencing technologies, after MPSS. The large quantities of data produced by DNA sequencing have also required development of new methods and programs for sequence analysis.

According to another embodiment of the present invention, the second cDNA strand is composed by: deoxyadenosine triphosphate (dATP), deoxyguanosine triphosphate (dGTP), deoxycytidine triphosphate (dCTP), deoxythymidine triphosphate (dTTP) and phosphorylated derivative thereof.

According to another embodiment of the present invention, the reads generated with said modified oligonucleotide primers are predominantly mapped to only the forward strand or the reverse strand of the generated double-stranded cDNA. As used herein, the term "predominantly" refers to a range above 90%, preferably above 95%.

According to a second aspect of the present invention, it is disclosed a kit for preparing strand-specific library from an RNA sample, wherein said kit comprises: random oligonucleotide primers comprising a 5' terminus nucleotide which allows no adaptor ligation, random oligonucleotide primers comprising a 5' terminus nucleotide which allows adaptor ligation, optionally a reverse transcriptase for synthesizing a first cDNA strand complementary to the template RNA, optionally dNTPs, optionally a DNA polymerase and optionally a ligase. In the context of the present application, the kit for preparing strand-specific library from an RNA sample may comprise or not dNTPs and/or DNA polymerase.

According to another embodiment of the second aspect of the present invention, the kit for preparing strand-specific library from an RNA sample does not require the presence of a polynucleotide kinase (PNK), e.g. T4 PNK.

The invention relates to a kit for preparing strand-specific library from an RNA sample wherein said oligonucleotide primers allowing adaptor ligation are 5'-phosphorylated oligonucleotides, and preferably wherein said oligonucleotide primers allowing adaptor ligation are 5'-adenylated oligonucleotides.

It also relates to a kit for preparing strand-specific library according from an RNA sample, wherein the reverse transcriptase is selected from a group consisting of: retroviral reverse transcriptase, retrotransposon reverse transcriptase, hepatitis B reverse transcriptase, cauliflower mosaic virus reverse transcriptase, murine leukemia virus reverse transcriptase, avian myeoloblastosis virus (AMV), bacterial reverse transcriptase, Tth DNA polymerase and Taq DNA polymerase.

According to a preferred embodiment of the second aspect of the present invention, one of the random oligonucleotide primers comprised in the kit is 5'-phosphorylated 5' adenylated oligonucleotide.

According to another embodiment of the second aspect of the present invention, the kit includes a reverse transcriptase which comprises: retroviral reverse transcriptase, retrotransposon reverse transcriptase, hepatitis B reverse transcriptase, cauliflower mosaic virus reverse transcriptase, murine leukemia virus reverse transcriptase, avian myeoloblastosis virus (AMV), bacterial reverse transcriptase, Tth DNA polymerase and Taq DNA polymerase.

EXAMPLES

The following experiment was performed to prove the principle of the method according to the present invention. The total RNA from Jurkat cells (human) were extracted with RNeasy kit (QIAGEN) and the PolyA+ mRNA was enriched with the GeneRead Pure mRNA Kit (QIAGEN) and then used in each RNA-Seq Library Prep reaction following the protocol below:

18 µl of mRNA (total amount: 72 ng) was mixed with 8 µl Reverse Transcription Buffer (250 mM Tris base, 15 mM $MgCl_2$, 375 mM KCl; final pH adjustment with HCl to pH 7.5) (5×), 2 µl random 8mer oligos (200 µM, IDT) and 2 µl $H_2O$. The mRNA/random oligo mix was heated at 94° C. for 15 minutes to fragment the RNA to an average size of about 100-250 bp. After the heat-mediated fragmentation, the mix was cooled down on ice and the following reverse transcription (RT) components were added: 2 µl of RNAse Inhibitor (4 U/µl, QIAGEN), 2 µl of dNTPs (10 mM each, QIAGEN), 4 µl of DTT (0.1 M), and 2 µl $H_2O$. The reaction volume was incubated for 2 minutes at 25° C. and 2 µl of qScript Reverse Transcriptase (200 U/µl, QIAGEN) was added to start the reverse transcriptase reaction. The following temperature profile was used for the RT reaction: 25° C. for 10 minutes, 42° C. for 50 minutes, and 70° C. for 15 minutes to inactivate the enzyme. Once the RT reaction was complete, the first strand cDNA synthesis reaction was purified with AMPure XP beads (Beckman Coulter) using a ratio of 1.8× beads to DNA volume (75.6 µl beads to 42 µl RT reaction).

Purified cDNA was subjected to second strand synthesis, which contained purified first strand cDNA (in 44.4 µl eluate) and either 4 µl (100 µM) modified random oligo primers ('Mod'/5Phos/NNN NNN NN, IDT) without 4 µl T4 Polynucleotide Kinase for the stranded protocol or 2 µl (200 µM) un-modified random primers ('Control', NNN NNN NN, IDT) with the addition of 4 µl T4 Polynucleotide Kinase (10 U/µl, Enzymatics) for the non-stranded control experiment.

The combination of modified random primers without T4 Polynucleotide Kinase established the strandness of the protocol. Sequencing adaptors can only be ligated with the cDNA generated in the second strand synthesis with 5' phosphate ends but not with cDNA generated in the reverse transcription without the 5' phosphate modification.

In addition, 8 µl (10×) Second Strand Synthesis Reaction Buffer (200 mM Tris-HCl pH 8, 100 mM $MgCl_2$, 120 mM $(NH_4)_2SO_4$, 1.6 mM β-NAD; final pH adjustment with HCl to pH 7.5), 4.8 µl DNA Polymerase I (5 U/µl, QIAGEN), 4 µl RNase H (5 U/µl, QIAGEN), 4 µl T4 DNA Polymerase (3 U/µl, QIAGEN), 1 µl of dNTPs (10 mM each, QIAGEN) and 9.8/7.8 µl of RNase-free water (QIAGEN) to make up the total reaction volume of 80 µl. The second-strand cDNA synthesis reaction was performed at 25° C. for 30 minutes and then heat-inactivated for 10 minutes at 70° C. The reaction mix was purified with AMPure XP beads (Beckman Coulter) using a ratio of 1.8× beads to DNA volume (144 µl beads to 80 µl RT reaction) and eluted in 25 µl water. 3 µl of Klenow (exo-) and 3 µl of 10× A-addition buffer (both from GeneRead Library Prep Kit, QIAGEN) were added to the 25 µl eluate and the A-addition reaction was performed at 37° C. for 30 minutes and inactivated at 75° C. for 10 minutes. The adaptor ligation reaction followed with GeneRead Library Adaptors for Illumina Sequencers (QIAGEN), the ligation buffer and ligase from the GeneRead Library Prep kit (QIAGEN) following manufacturer's instructions. The ligated sequencing library was purified with two rounds of AMPure XP bead purifications (Beckman Coulter) using a ratio of 0.8× beads to DNA volume (72 µl beads to 90 µl RT reaction) and PCR-amplified for 10 cycles (GeneRead Library Amplification kit, QIAGEN).

Both libraries were then sequenced on MiSeq instrument with the MiSeq Reagent Kit V3 (150 nt) in paired-end sequencing. Sequencing data were mapped with the STAR aligner (Dobin et al. 2013, Bioinformatics 29 (1):15-21). Strandness was assessed with the infer_experiment.py script included in the RSeQC package (RNA-seq Quality control package, Wang et al. 2012, Bioinformatics 28 (16):2184-2185) and TPM transcript expression was analyzed with RSEM (RNA-Seq by Expectation-Maximization; Li and Dewey 2011, BMC Bioinformatics 12:323).

Figure 2:
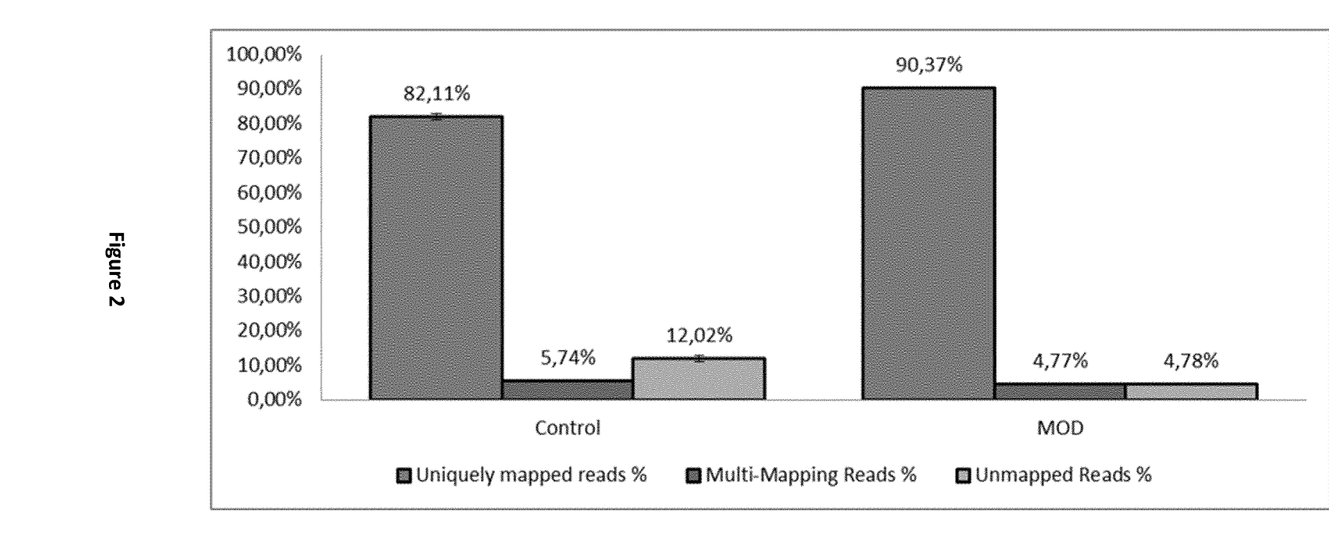
FIG. 2 shows the high percentage of uniquely mapped reads with both control ('Control') and stranded ('MOD') RNA sequencing libraries.

As shown in FIG. 2, both libraries had high percentage of reads that were mapped uniquely to human genome reference hg38 with better results for the stranded "MOD" protocol (82.11% and 90.37%), as well as low numbers of multi-mapping reads (5.74% and 4.77%) and unmapped reads (12.02% and 4.78%) demonstrating good library quality, especially for the stranded protocol (n=2 with standard deviation).

Figure 3:
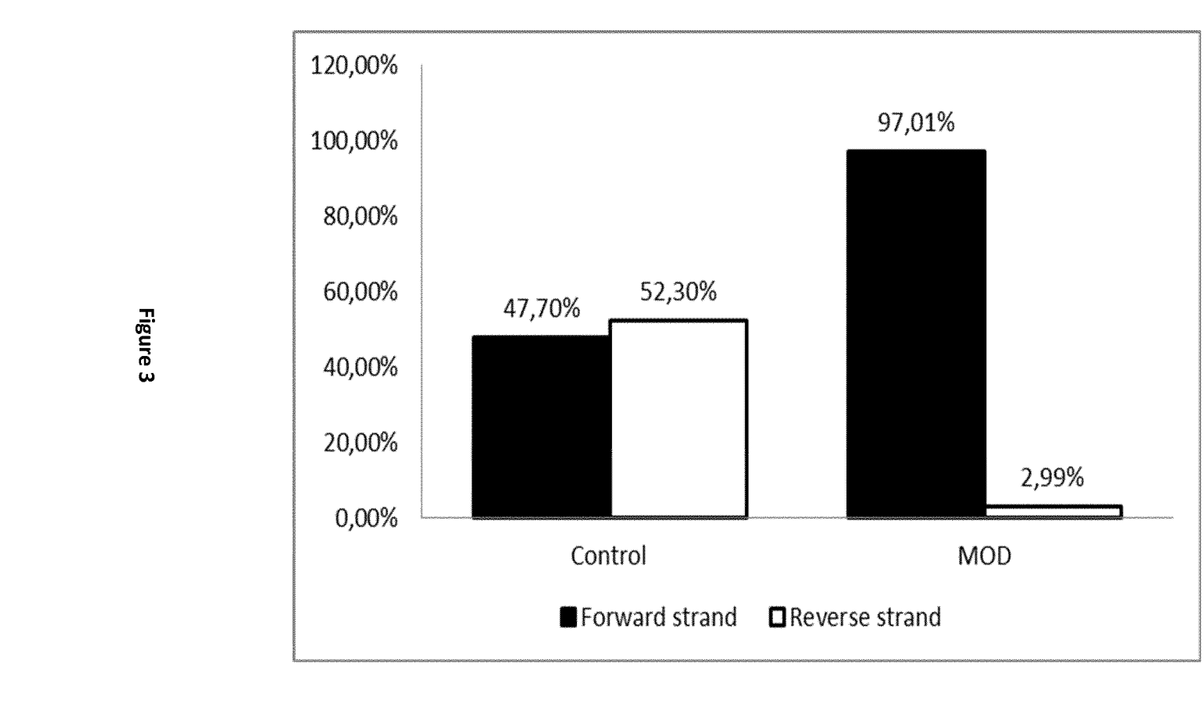
FIG. 3 shows the strand specificity of the RNA sequencing libraries. In particular, the figure shows the percentage of reads mapped to the forward or reverse strand of the reference.

The strand specificity of both libraries has been examined. As shown in FIG. 3, the reads generated with 5' modified random oligos (MOD) are predominantly mapped to the forward strand of the reference, while only a small portion of reads could be mapped to the reverse strand. In contrast, the mapping for control library reads is relatively balanced for forward vs reverse strand (n=2 with standard deviation).

What is claimed is:

1. A method for preparing a strand-specific library from a nucleic acid sample, the method comprising the steps of:
   i. generating a plurality of first nucleic acid strands by subjecting a fragmented nucleic acid to a first strand specific amplification by using first oligonucleotide primers,
   ii. generating a plurality of second nucleic acid strands by strand specific elongation using second oligonucleotide primers and the plurality of first nucleic acid strands as a template to form a double-stranded nucleic acid,
   wherein said second oligonucleotide primers comprise a modification at their 5' terminal nucleotide, and
   iii. ligating an adapter to the 3' and 5' termini of the double-stranded nucleic acid generated in step ii,
   wherein the first strand allows no adapter ligation at its 5' terminus and said second strand allows adapter ligation at its 5' terminus and,
   iv. optionally cloning, sequencing or otherwise using the strand-specific library.

2. The method according to claim 1, wherein the oligonucleotide primers comprise DNA, RNA or modified nucleotides.

3. The method according to claim 1, wherein the oligonucleotide primers are random oligonucleotide primers.

4. The method according to claim 1, wherein the first and/or second oligonucleotide primers comprise a phosphate, adenylation group (App), phosphorothioate, phosphoroselenoate group or a derivative thereof.

5. The method according to claim 1, wherein the second oligonucleotide primers are 5'-phosphorylated oligonucleotides.

6. The method according to claim 1, wherein the oligonucleotide primers are between 4 and 30 bases in length.

7. The method according to claim 1, wherein the library is sequenced and sequencing reads generated with said second oligonucleotide primers are predominantly only mapped to the second strand of the generated double-stranded nucleic acid.

8. The method for preparing a strand-specific library from a nucleic acid sample, wherein the sample is an RNA sample, the method comprising the steps of:
   i. generating a plurality of first cDNA strands by subjecting a fragmented RNA to reverse transcription by using a reverse transcriptase and first oligonucleotide primers, wherein said first oligonucleotide primers comprise a modification at their 5' terminal nucleotide,
   ii. generating a plurality of second cDNA strands by using a DNA polymerase, second oligonucleotide primers, and the plurality of first cDNA strands as a template to form a double-stranded cDNA, and
   iii. ligating an adapter to the 3' and 5' termini of the double-stranded cDNA generated in step ii,
   wherein the first cDNA strand allows adapter ligation at its 5' terminus and said second cDNA strand allows no adapter ligation at its 5' terminus and,
   v. optionally cloning, sequencing or otherwise using the strand-specific library.

9. The method according to claim 8, wherein said RNA sample is extracted from a eukaryotic organism.

10. The method according to claim 8, wherein said RNA sample comprises polyadenylated mRNA.

11. The method according to claim 8, comprising an RNA sample fragmenting step that produces fragmented RNA of between 100 bp to 500 bp in size.

12. The method according to claim 8, wherein said RNA sample is fragmented by thermal, chemical, enzymatic means or a combination thereof.

13. The method according to claim 8, wherein the modification is a phosphorylation at the 5' terminus.

* * * * *